United States Patent [19]

Grundei

[11] Patent Number: 5,129,880
[45] Date of Patent: Jul. 14, 1992

[54] PENIS PROSTHESIS

[76] Inventor: Hans Grundei, Industriestrass 2, D-6222 Geisenheim, Fed. Rep. of Germany

[21] Appl. No.: 613,206

[22] Filed: Nov. 14, 1990

[30] Foreign Application Priority Data

Feb. 9, 1990 [DE] Fed. Rep. of Germany ... 9001508[U]

[51] Int. Cl.$^5$ ............................................. A61F 2/26
[52] U.S. Cl. ..................................................... 600/40
[58] Field of Search .......................................... 128/79

[56] References Cited

U.S. PATENT DOCUMENTS

| | | | |
|---|---|---|---|
| 4,267,829 | 5/1981 | Burton et al. | 128/79 |
| 4,411,260 | 10/1983 | Koss | 128/79 |
| 4,718,410 | 1/1988 | Hakky | 128/79 |
| 4,881,530 | 11/1989 | Trick | 128/79 |

*Primary Examiner*—Cary E. O'Connor
*Attorney, Agent, or Firm*—Gifford, Groh, Sprinkle, Patmore & Anderson

[57] ABSTRACT

A penis prosthesis comprises an implantable plastic rod member having an erection chamber which can be filled by a fluid under pressure, and a hose connection communicating with the erection chamber for expansion thereof. The erection chamber is in the middle portion of the prosthesis and is closed outwardly by a sleeve portion which joins front and rear portions of the prosthesis together and which can be extended in length when the erection chamber is pressurized.

16 Claims, 1 Drawing Sheet

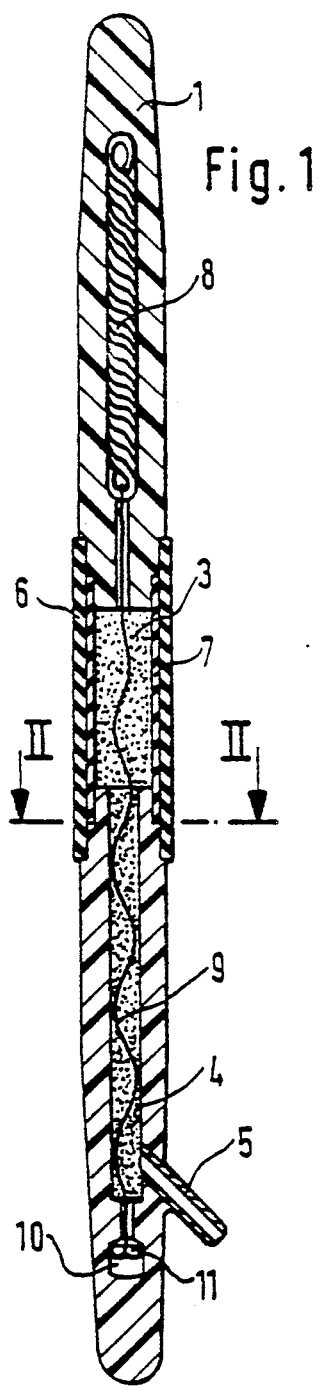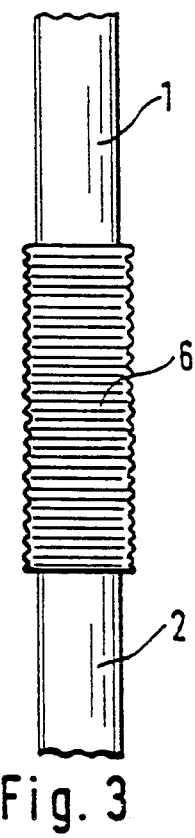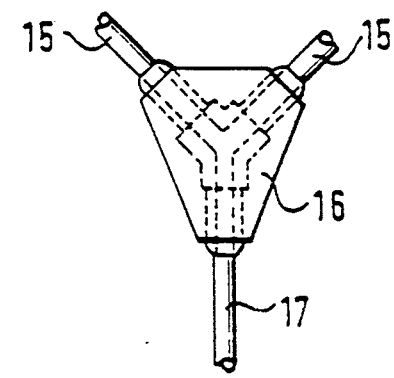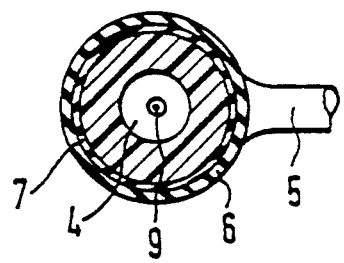

PENIS PROSTHESIS

BACKGROUND OF THE INVENTION

Various forms of penis prosthesis have been developed, for example comprising an implantable rod member of plastic material which can be bent into the respectively desired shape by virtue of the provision of an insert of fine silver wires in the form of a braided component, as disclosed for example in DE-U-83 35133.7. Another form of penis prosthesis comprises an implantable rod member which is made from plastic material and which includes an erection chamber that can be filled with a fluid under pressure, and a hose connection communicating with the erection chamber. In the rest condition, such a prosthesis is bendable and flaccid. When the erection chamber container contained in the prothesis, in the form of a tubular cavity, is put under pressure by the introduction of a fluid, for example by means of a small pump which is also implanted, the prosthesis expands and at the same time becomes stiff. The prosthesis is returned to its rest condition by releasing the pressure from the returned to its rest condition by releasing the pressure from the erection chamber, by the actuation of a suitable valve.

SUMMARY OF THE INVENTION

An object of the present invention is to provide a penis prosthesis which more closely approximates to the normal development of the erection of a natural penis.

Another object of the present invention is to provide a penis prosthesis which is reliable and simple to operate.

In accordance with the principles of the present invention, these and other objects are achieved by a penis prosthesis in the general form of an implantable rod member made from plastic material and comprising an erection chamber adapted to be filled with a fluid under pressure, and a hose connectiong communicating with the erection chamber. The erection chamber is arraged in a central portion of the rod member and is closed off outwardly by a sleeve portion which can be extended in respect of its length and which joints together front and rear portions of the rod member, at respective sides of the erection chamber.

As will be seen in greater detail from a preferred embodiment of the invention as described hereinafter, when the erection chamber is filled with fluid under pressure, the sleeve portion increases in length so that the prosthesis overall also becomes longer. That imitates the natural procedure involved in an erection, which, besides producing a stiffening effect, also produces an increase in the length of the penis.

In accordance with a preferred feature of the invention, the sleeve portion can be designed in the nature of a bellows. As a tried and tested item in that respect, it is possible to use vessel prostheses which are employed to a large extent for the replacement in particular of veins in the human body. A stretchable sealing tube for the erection chamber may advantageously be disposed in the interior of the sleeve portion, to provide an improved sealing effect.

In another preferred feature of the invention, the front portion of the rod member, which therefore constitutes the distal portion in the implanted condition of the prosthesis, includes a stiffening insert. A stiffening insert may also be embedded in the rear portion of the rod member, which therefore consitutes the proximal portion. The stiffening insert may comprises fine twisted silver wires which thus form a braided component. In order to increase the strength of the stiffening insert, even after a larger number of bending operations carried out thereon, the individual wires may be individually embedded into a shrink tube.

In order to ensure that the prosthesis does not suffer from an unacceptably great increase in length when the erection chamber is subjected to a high fluid pressure, another preferred feature of the invention provides that the front and rear portions of the prosthesis are connected together by a flexible element such as a thread to limit the longitudinal extension of the prosthesis. The thread which may comprise for example nylon is desirably fixed to the stiffening insert in the front portion of the prosthesis, and extends through the erection chamber to an anchorage point in the rear or proximal portion of the prothesis.

Preferably, the portions of the rod member and the sleeve portion comprise silicone of a quality which is accepted for implantation purposes. The individual parts of the prosthesis are secured together by adhesive.

Preferably, prostheses are implanted in pairs and are inserted into the erectily tissue.

Further objects, features and advantages of the invention will be apparent from the following description of a preferred embodiment thereof.

BRIEF DESCRIPTION OF THE DRAWING

FIG. 1 is a view in longitudinal section through an embodiment of a penis prosthesis according to the invention, FIG. 2 is a view on an enlarged scale of the prosthesis shown in FIG. 1, in cross-section taken along line II—II in FIG. 1, FIG. 3 is a view of the central region of the penis prosthesis shown in FIGS. 1 and 2, and FIG. 4 is a distribution portion for distribution of pressure fluid to the two prosthesis rod members of an implanted pair.

DESCRIPTION OF THE PREFERRED EMBODIMENT

Referring to the drawing and more especially FIG. 1 thereof, illustrated therein is a penis prosthesis according to the invention comprising a front portion 1 which constitutes the distal portion of the prosthesis and a rear portion 2 which constitutes the proximal portion. The portions 1 and 2 are made from a suitable material such as silicon. In the central region of the penis prosthesis is an erection chamber which is generally indicated by reference numeral 3 and which is communicated by way of a bore 4 in the rear portion 2 with a hose connection 5. The erection chamber 3 is closed off outwardly by a sleeve portion 6 which can be in the form of a bellows. A thin-walled stretchable sealing tube 7 is arranged on the inside of the sleeve portion 6 to provide a better sealing effect for the erection chamber 3. Both the tube 7 and the sleeve portion 6 are joined to the front portion 1 and the rear portion 2 by adhesive, with the respective ends of the tube 7 and the sleeve portion 6 being accommodated in suitable recesses provided in the peripheral surfaces of the respective portions 9 and 2 at the ends thereof adjacent the erection chamber 3.

Disposed in the front portion 1 of the rod member is a braided component 8 formed from twisted fine silver wires which are individually disposed in shrink tubes. The braided component 8 provides for stiffening of the front portion 1 of the prosthesis and permits it to be put into an appropriate shape by bending thereof. As the wires of the braided component 8, which comprise high-purity silver, have practically no resilient return effect, the portion 1 of the rod member remains in the respective bent shape into which it has been put.

Secured to the rearward end of the braided component 8 is a thread 1 of for example nylon which extends through the erection chamber 3 and the bore 4 in the rear portion 2 of the prosthesis to a fixing location indicated at 10 in the rear portion 2 of the rod member. The fixing location 10 is formed by a small chamber which accommodates a metal portion 11 for fixing of the thread 9 thereto. Instead of a separate metal member 11, it would also be possible to knot the thread 9 for the purposes of anchoring it in the chamber 10.

The rod members illustrated are preferably implanted in pairs and, after the implantation of the two rod members, two hoses (not shown) are fitted on to the two connections 5 and taken to the connections 15 of the Y-type branch connector 16 shown in FIG. 4, which is implanted under the skin in the region of the base of the penis. A further hose (not shown) the goes from the connection 17 of the connector 16 to a pump (also not shown) which is implanted under the skin for example in the region of the groin fold. The pump may be for example a pump which is actuated by finger pressure, with a check valve, and a reservoir for the fluid, preferably a physiological saline solution. When the fluid is pumped into the erection chamber 3 under pressure, the sleeve portion 6 is expanded together with the tube 7 in the longitudinal direction of the prosthesis so that the rod member stiffens and also increases in length. In addition there can be a limited increase in diameter in the region of the erection chamber 3 and the lower portion 2 of the rod member.

The pump will desirably have a pressure reliev valve in order to limit the maximum pressure which can be attained. In addition the arrangement may have a relief valve which can also be actuated through the skin of the patient and which permits the fluid to flow back into the pump reservoir. It will be appreciated that, instead of a hand-operated pump, it is also possible to use a pump which is actuated by an electric motor.

It will be appreciated that the above-described construction has been set forth solely by way of example and illustration of the principles of the present invention and that various modifications and alterations may be made therein without thereby departing from the spirit and scope of the invention.

What is claimed is:

1. A penis prosthesis in the form of an implantable rod member of plastic material, said implantable rod member comprising; a front portion; a rear portion; a sleeve portion disposed substantially between said front and rear portions, said sleeve portion surrounding an erection chamber adapted to be filled with a pressurized fluid, said sleeve portion being extendable with respect to its length; a hose connection communicating with said erection chamber; and a nonresilient bendable insert provided in said front portion permitting said front portion to be bent into an appropriate shape.

2. The penis prosthesis as set forth in claim 1 wherein said sleeve portion has bellows configuration.

3. The penis prosthesis as set forth in claim 1 including a stretchable sealing tube disposed in the interior of said sleeve portion.

4. The penis prosthesis as set forth in claim 3 wherein said front and rear portions of said rod member, said sleeve portion and said sealing tube are secured together by an adhesive.

5. The penis prosthesis as set forth in claim 1 wherein said bendable insert is embedded in at least one of said front and rear portions of said rod member.

6. The penis prosthesis as set forth in claim 5 wherein said bendable insert includes twisted fine silver wires.

7. The penis prosthesis as set forth in claim 1 comprising a flexible means connecting said front portion and said rear portion of said rod member together to limit the longitudinal extension of said prosthesis upon pressurization of said erection chamber.

8. The penis prosthesis as set forth in claim 7 wherein said flexible means is a thread.

9. A penis prosthesis in the form of an implantable rod member comprising: a front portion adapted to constitute a distal portion of said prosthesis; a rear portion adapted to constitute a proximal portion of said prosthesis; a sleeve portion constituting a central part of the length of said prosthesis and connecting said first and second portions together, said sleeve portion defining therebetween a lengthwise extendable erection chamber adapted to be filled with a pressurized fluid to increase the length of said erection chamber and therewith the length of said prosthesis; a nonresilient bendable insert provided in said front portion permitting said front portion to be bent into an appropriate shape, a bore in said rear portion of said rod member having a first end communicating with said erection chamber and a second end opening to the exterior of said rod member; and means for applying a source for said pressurized fluid through said bore and into said erection chamber.

10. The penis prosthesis as set forth in claim 9 wherein said sleeve portion has a bellows configuration.

11. The penis prosthesis as set forth in claim 9 including a stretchable sealing tube disposed in the interior of said sleeve portion.

12. The penis prosthesis as set forth in claim 11 wherein said front and rear portions of said rod member, said sleeve portion and said sealing tube are secured together by an adhesive.

13. The penis prosthesis as set forth in claim 9 wherein said bendable insert includes twisted fine silver wires.

14. The penis prosthesis as set forth in claim 9 comprising a flexible means connecting said front portion and said rear portion of said rod member together to limit the longitudinal extension of said prosthesis upon pressurization of said erection chamber.

15. The penis prosthesis as set forth in claim 14 wherein said flexible means is a thread.

16. A penis prosthesis having an implantable rod member of plastic material comprising:
   a front portion;
   a rear portion;
   a sleeve portion disposed substantially between said front and rear portions, said sleeve portion defining an erection chamber adapted to be filled with a pressurized fluid, said sleeve portion being extendable with respect to its length,
   a flexible thread connecting said front portion and said rear portion together to limit the longitudinal extension of said prosthesis upon pressurization of said erection chamber, a stiffening insert placed centrally within said front portion, said flexible thread being fixed to said stiffening insert at one end, said flexible thread extending through said erection chamber and being fixed to an anchorage means in said rear portion at another end, and a hose connected to said erection chamber.

* * * * *